United States Patent
Nakamura

(10) Patent No.: US 7,388,082 B2
(45) Date of Patent: Jun. 17, 2008

(54) ALKOXYALCOHOL ADDUCT OF RARE EARTH MONOCARBOXYLATE

(75) Inventor: Shigeru Nakamura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 30 days.

(21) Appl. No.: 11/226,310

(22) Filed: Sep. 15, 2005

(65) Prior Publication Data

US 2006/0054871 A1    Mar. 16, 2006

(30) Foreign Application Priority Data

Sep. 15, 2004    (JP)    ............................ 2004-268804

(51) Int. Cl.
    *C07F 5/00*    (2006.01)
(52) U.S. Cl. ........................................... 534/16; 534/15
(58) Field of Classification Search .............. 252/521.1; 560/66; 562/6; 501/78; 534/16, 15
    See application file for complete search history.

(56) References Cited

U.S. PATENT DOCUMENTS 4,425,278 A * 1/1984 Wirth et al. .................... 534/11

OTHER PUBLICATIONS

Alain Lebrun, Jean-Louis Namy and Henri B. Kagan A New Preparation of Lanthanide Alkoxides, and some Applications in Catalysis. Tetrahedron Letters, vol. 32, No. 21, pp. 2355-2358, 1991.*

* cited by examiner

*Primary Examiner*—Elvis O Price
(74) *Attorney, Agent, or Firm*—Sughrue Mion, PLLC

(57) ABSTRACT

An alkoxyalcohol adduct of rare earth monocarboxylate has the formula (I):

$$M(R^2-COO)_3 \cdot (R^1O(CH_2)_nOH)_p \quad (I)$$

in which M is a rare earth element such as Pr, Nd, Pm, Sm, Eu, Gd, Tb, Dy, Ho, Er, Tm, Yb and Lu; $R^1$ is an aliphatic hydrocarbon group having 1 to 4 carbon atoms or a substituted aliphatic hydrocarbon group having 3 to 6 carbon atoms; $R^2$ is a hydrogen atom or an aliphatic hydrocarbon group having 1 to 4 carbon atoms which has or does not have a substituent; n is 2 or 3; and p is a number in the range of 0.5 to 3.

4 Claims, No Drawings

ALKOXYALCOHOL ADDUCT OF RARE EARTH MONOCARBOXYLATE

FIELD OF THE INVENTION

The present invention relates to a new alkoxyalcohol adduct of rare earth monocarboxylate. The adduct is a useful material for producing rare earth oxides and compound oxides comprising a rare earth element.

BACKGROUND OF THE INVENTION

Rare earth oxides and compound oxides comprising rare earth elements are widely used as functional inorganic materials such as phosphor, solid electrolyte, superconducting membrane, catalyst, ceramics and optical glass. For producing the rare earth oxides, rare earth alkoxides have been conventionally used as precursory material.

JP-A-7-285969 discloses a process for preparation of a rare earth alkoxyalkoxide. There are, however, some problems in this process. In the disclosed process, a rare earth carboxylate is caused to react with an alkali metal alkoxyalcoholate. As the alkali metal alkoxyalcoholate (namely, as a starting material of the process), an unstable alkali metal alkoxyalkoxide such as sodium alkoxyalkoxide is used. In addition, it is difficult to isolate and remove alkali metal carboxylate, that is a by-product of the reaction. Further, the rare earth carboxylate, that is another starting material of the process, must be beforehand made anhydrous. It is known that a pure anhydrous rare earth carboxylate can not be easily obtained by a simple procedure. If heated to dry by normal procedure, the hydrated rare earth carboxylate often decomposes.

Leblanc et al. [Tetrahedron Letters, vol. 32(1991), No. 21, pp. 2355-2358] disclose a process for preparation of a rare earth isopropoxide. In the process, a hydrated rare earth carboxylate is successively reacted with orthoformate, with 2-propanol and with n-butyl lithium. In this process lithium chloride is formed as a by-product. The lithium chloride precipitates in the form of very fine crystallite which is not easily separated from the product by filtration, and hence is liable to remain in the filtrate together with the product. Accordingly, in order to obtain a pure rare earth isopropoxide, it is necessary to repeat the purification procedures. As a result, troublesome procedures are indispensable, and the production yield is often low.

IEEE Transactions on Nuclear Science, vol. 47(2000), No. 6, pp. 1781-1786 discloses a process for preparation of lutetium isopropoxide. In the process, lutetium metal and isopropanol are reacted under nitrogen gas atmosphere in the presence of mercury chloride (catalyst). This process, however, has some problems. The mercury compound is harmful to the environment, and the rare earth metal is so expensive and so easily oxidized that it has to be treated very carefully.

SUMMARY OF THE INVENTION

An object of the present invention is to provide a new alkoxyalcohol adduct of a rare earth monocarboxylate. This adduct is a useful material for producing rare earth oxides and compound oxides comprising rare-earth element.

The invention resides in an alkoxyalcohol adduct of rare earth monocarboxylate, represented by the formula (I):

$$M(R^2-COO)_3 \cdot (R^1O(CH_2)_nOH)_p \quad (I)$$

in which M is at least one rare earth element selected from the group consisting of Pr, Nd, Pm, Sm, Eu, Gd, Tb, Dy, Ho, Er, Tm, Yb and Lu; $R^1$ is an aliphatic hydrocarbon group having 1 to 4 carbon atoms or a substituted aliphatic hydrocarbon group having 3 to 6 carbon atoms; $R^2$ is a hydrogen atom or an aliphatic hydrocarbon group having 1 to 4 carbon atoms which has or does not have a substituent; n is 2 or 3; and p is a number in the range of 0.5 to 3.

The above-identified adduct of the invention can be easily prepared by the process comprising the step of:

heating a rare earth carboxylate represented by the formula (II):

$$M(R^2-COO)_3 \cdot mH_2O \quad (II)$$

[in which M and $R^2$ are the same as those defined above, and m is a number satisfying the condition of $0 \leq m \leq 4$]

together with an alkoxyalcohol represented by the formula (III):

$$R^1-O-(CH_2)_nOH, \quad (III)$$

[in which $R^1$ and n are the same as those defined above], to remove water together with the alkoxyalcohol by distillation.

The alkoxyalcohol adduct of rare earth monocarboxylate provided by the invention can be easily prepared, and is very useful for producing rare earth oxides and compound oxides comprising rare earth element.

DETAILED DESCRIPTION OF THE INVENTION

In the above formula, $R^2$ is preferably methyl. The alkoxyalcohol represented by the formula (III) is preferably at least one compound selected from the group consisting of 2-methoxyethanol, 2-ethoxyethanol, 1-methoxy-2-propanol, 1-ethoxy-2-propanol and 3-ethoxy-1-propanol. It is particularly preferred in the process of the invention to heat rare earth acetate together with ethoxyethanol so that water is distilled away together with the solvent (alkoxyalcohol).

The process for preparation of the adduct according to the invention is described below in more detail.

The rare earth carboxylate, which is a starting material of the process, is represented by the following formula (II):

$$M(R^2-COO)_3 \cdot mH_2O \quad (II)$$

[in which M is at least one rare earth element selected from the group consisting of Pr, Nd, Pm, Sm, Eu, Gd, Tb, Dy, Ho, Er, Tm, Yb and Lu; $R^2$ is a hydrogen atom or an aliphatic hydrocarbon group having 1 to 4 carbon atoms which has or does not have a substituent; and m is a number satisfying the condition of $0 \leq m \leq 4$].

The rare earth carboxylate is preferably formate, acetate or propionate; more preferably formate or acetate. The carboxylate may be either hydrated or anhydrous salt.

The rare earth carboxylate can be synthesized according to known methods. Before the process for preparing the adduct of the invention, the rare earth carboxylate can be synthesized in a reaction container. If this is the case, the synthesized carboxylate can be successively used in the process of the invention. For example, a rare earth oxide or hydroxide is dissolved in an aqueous acetic acid solution, and then the excess acetic acid and water are distilled off to prepare the rare earth acetate.

The alkoxyalcohol is represented by the following formula (III):

$$R^1-O-(CH_2)_nOH, \quad (III)$$

[in which $R^1$ is an aliphatic hydrocarbon group having 1 to 4 carbon atoms or a substituted aliphatic hydrocarbon group having 3 to 6 carbon atoms; and n is 2 or 3].

The alkoxyalcohol is preferably 2-methoxyethanol, 2-ethoxyethanol, 1-methoxy-1-propanol, 1-ethoxy-2-propanol, 3-ethoxy-1-propanol, 2-(2-ethoxyethoxy)ethanol, 2-(2-methoxyethoxy)ethanol, acetoxyethanol, 2-isopropoxyethanol or 2-butoxyethanol; more preferably 2-methoxyethanol, 2-ethoxyethanol, 1-methoxy-2-propanol, 1-ethoxy-2-propanol or 3-ethoxy-1-propanol; most preferably 2-ethoxyethanol.

The amount of alkoxyalcohol generally is 3 mol. or more, preferably 10 mol. or more, more preferably in the range of 30 to 1,000 mol., per 1 mol. of the rare earth carboxylate. If the alkoxyalcohol is in an amount of 10 mol. or less per 1 mol. of the rare earth carboxylate, a compatible solvent such as non-substituted alcohol (e.g., ethanol, isopropanol, butanol) or acetonitrile can be used as an auxiliary solvent. It is, however, preferred to use singly a large excess of an alkoxyalcohol so that the alkoxyalcohol can serve not only as a reactant but also as a solvent.

At the first stage of the process, the rare earth carboxylate is dispersed and mixed in the alkoxyalcohol, to prepare a mixture. The solvent of the mixture may be the alkoxyalcohol alone, a mixed solvent thereof with a low boiling point-alcohol or a mixed solvent thereof with water. For example, a powdery rare earth acetate is added to the solvent, or otherwise an aqueous solution in which rare earth acetate is beforehand dissolved is added to the solvent.

The mixture is then heated and a portion of the mixture is distilled off. The mixture is heated generally at atmospheric pressure, but can be heated and partly distilled off under reduced pressure. In an ordinary embodiment of the process, the mixture is heated to the boiling point of the solvent and refluxed to accelerate the reaction. However, as long as the reaction proceeds, the temperature may be below the boiling point. For example, the mixture is heated and refluxed at 135° C. or 145° C. (external temperature of the reaction container) if the alkoxyalcohol is methoxyethanol or ethoxyethanol, respectively. While being refluxed, the mixture is partly distilled off to remove waste produced in the reaction mixture. For performing the distillation, the reaction container can be equipped with a rectification column. Otherwise, dry nitrogen gas can be introduced into the reaction container so as to remove the waste in the form of vapor together with vapor of the alkoxyalcohol. The amount of the reaction mixture distilled off depends on nature of the rare earth element and the composition of the reaction mixture, but generally is in the range of 10% to 50% of the reaction mixture. As the reaction proceeds, the reaction mixture varies from an opaque suspension to a transparent solution. This variation indicates completion of the reaction.

Since the alkoxyalcohol used in the invention has a higher boiling point than water, water contained in the solvent and crystal water of the carboxylate are distilled off when heated. At the same time, the starting materials are combined to form a soluble alkoxyalcohol adduct of rare earth monocarboxylate. In this way, an alkoxyalcohol solution containing the desired adduct can be obtained. The excess of the alkoxyalcohol can be further distilled off to isolate the alkoxyalcohol adduct represented by the formula (I). According to the use of the prepared adduct, the obtained alkoxyalcohol solution can be directly used without isolating the adduct. The obtained adduct or the solution can be used as the material for producing thin films, fibers or a powder of rare earth oxide.

EXAMPLE 1

Ethoxyethanol Adduct of Lutetium Acetate

In a three necked-flask, 16.5 g of lutetium acetate tetrahydrates was dispersed in 500 mL of ethoxyethanol. While being stirred with a stirrer, the mixture was heated and refluxed on an oil bath at atmospheric pressure for 7 hours. Under refluxing, approx. 100 mL of a solvent mixture was distilled off through a rectification column. The reaction mixture gradually varied into a pale yellow transparent solution. The reaction mixture was transferred into an egg-plant type flask in a stream of dry nitrogen gas, an the solvent was distilled off under 15 mmHg at 75° C. to 95° C. by means of a rotary evaporator. Thus, a pale yellow viscous liquid was obtained.

The product was analyzed according to Fourier transform infrared spectroscopy, and the obtained spectrum showed signals assignable to acetic group and ethoxyethanol. The elemental analysis of the product was also carried out, and the results were set forth in Table 1. As shown in Table 1, the results of the analysis correspond well to the composition of the target ethoxyethanol adduct of lutetium acetate. The yield was 98%. Further, metal elements contained in the resulting product were analyzed. The analysis indicated that, although approx. 20 ppm of Ca, which was originally contained in the lutetium acetate (starting material), was detected, no metals were detected over the detection limit.

TABLE 1

| | | Elemental analysis (%) | | | | | | | |
|---|---|---|---|---|---|---|---|---|---|
| | Yield | Found | | | | Calculated | | | |
| Product | (%) | Lu | C | H | O | Lu | C | H | O |
| $Lu(CH_3COO)_3.(C_2H_5OC_2H_4OH)_{1.2}$ | 98 | 38.0 | 28.2 | 4.6 | 29.2 | 38.0 | 26.9 | 4.5 | 28.7 |

EXAMPLE 2

Ethoxyethanol Adduct of Rare Earth Acetate

Each rare earth acetate in each amount shown in Table 2 was dispersed in 100 mL of ethoxyethanol, and the mixture was heated and refluxed on an oil bath equipped with a stirrer at 145° C. under atmospheric pressure. The reaction period of each reaction is also set forth in Table 2. The mixture of each rare earth element other than lanthanum and cerium turned into a yellowish transparent solution as the reaction proceeded. From the obtained solution, the solvent was distilled off in the same manner as in Example 1 to prepare a viscous liquid product.

The elemental analysis and the yield of each product are set forth in Table 3 (in which EEA stands for $C_2H_5OC_2H_4OH$).

TABLE 2

| Material | Amount (g) | Reaction period (hour) |
|---|---|---|
| $Pr(CH_3COO)_3.H_2O$ | 3.9 | 3.5 |
| $Nd(CH_3COO)_3.H_2O$ | 3.9 | 1.0 |
| $Sm(CH_3COO)_3.4H_2O$ | 4.0 | 1.0 |
| $Eu(CH_3COO)_3.4H_2O$ | 4.0 | 1.0 |
| $Gd(CH_3COO)_3.4H_2O$ | 4.1 | 1.0 |
| $Tb(CH_3COO)_3.4H_2O$ | 4.1 | 0.5 |
| $Dy(CH_3COO)_3.4H_2O$ | 4.1 | 6.0 |
| $Ho(CH_3COO)_3.4H_2O$ | 4.1 | 5.0 |
| $Er(CH_3COO)_3.4H_2O$ | 4.2 | 2.0 |
| $Tm(CH_3COO)_3.4H_2O$ | 4.2 | 3.0 |
| $Yb(CH_3COO)_3.4H_2O$ | 4.2 | 4.0 |

TABLE 3

| Product | Yield (%) | Calculated C | H | O | M | Found C | H | O | M |
|---|---|---|---|---|---|---|---|---|---|
| $Pr(CH_3COO)_3.(EEA)_{1.5}$ | 98 | 31.8 | 5.2 | 31.8 | 31.1 | 31.6 | 5.1 | 31.6 | 29.5 |
| $Nd(CH_3COO)_3.(EEA)_{1.1}$ | 97 | 29.7 | 4.8 | 31.2 | 34.3 | 28.8 | 4.8 | 30.5 | 33.5 |
| $Sm(CH_3COO)_3.(EEA)_{1.1}$ | 98 | 29.3 | 4.7 | 30.8 | 35.2 | 28.7 | 4.7 | 30.0 | 33.8 |
| $Eu(CH_3COO)_3.(EEA)_{0.9}$ | 99 | 28.1 | 4.4 | 30.4 | 37.0 | 27.0 | 4.3 | 30.1 | 36.1 |
| $Gd(CH_3COO)_3.(EEA)_{1.1}$ | 97 | 28.8 | 4.7 | 30.3 | 36.3 | 28.6 | 4.5 | 28.9 | 35.1 |
| $Tb(CH_3COO)_3.(EEA)$ | 97 | 28.2 | 4.5 | 30.0 | 37.3 | 27.0 | 4.5 | 29.2 | 35.5 |
| $Dy(CH_3COO)_3.(EEA)$ | 96 | 27.9 | 4.5 | 29.8 | 37.8 | 27.8 | 4.3 | 29.5 | 37.7 |
| $Ho(CH_3COO)_3.(EEA)_{0.9}$ | 97 | 27.2 | 4.3 | 29.5 | 39.0 | 27.1 | 4.2 | 29.0 | 38.0 |
| $Er(CH_3COO)_3.(EEA)$ | 98 | 27.6 | 4.4 | 29.5 | 38.5 | 27.5 | 4.3 | 29.0 | 37.8 |
| $Tm(CH_3COO)_3.(EEA)_{2.0}$ | 98 | 27.5 | 4.4 | 29.3 | 38.7 | 27.1 | 4.4 | 29.1 | 38.7 |
| $Yb(CH_3COO)_3.(EEA)_{0.9}$ | 97 | 26.7 | 4.2 | 28.9 | 40.1 | 25.9 | 4.0 | 27.8 | 39.2 |

EXAMPLE 3

Preparation of Terbium-activated Lutetium oxide phosphor

The ethoxyethanol adduct of lutetium acetate prepared in Example 1 in the amount of 27 g was dissolved in 100 ml of beforehand-dehydrated ethoxyethanol. After 280 μL of 0.1 mol/L ethanol solution of terbium nitrate was added, the solution was heated and refluxed. The solvent was distilled off by means of a rotary evaporator, to obtain a transparent viscous gel. After being crushed in a mortar, the gel was put in an aluminum crucible and then fired at 1,200° C. for 4 hours to obtain a white powdery terbium-activated lutetium oxide phosphor.

The obtained phosphor gave a strong green emission when excited with ultraviolet rays, and the intensity of the emission was approximately twice as strong as that emitted by a phosphor obtained by firing a mixture of the corresponding oxides in the same manner.

What is claimed is:

1. A process for preparation of an alkoxyalcohol adduct of rare earth monocarboxylate, represented by the formula (I):

$$M(R^2-COO)_3.(R^1O(CH_2)_nOH)_p \quad (I)$$

in which M is at least one rare earth element selected from the group consisting of Pr, Nd, Pm, Sm, Eu, Gd, Tb, Dy, Ho, Er, Tm, Yb and Lu; $R^1$ is an aliphatic hydrocarbon group having 1 to 4 carbon atoms or a substituted aliphatic hydrocarbon group having 3 to 6 carbon atoms; $R^2$ is a hydrogen atom or an aliphatic hydrocarbon group having 1 to 4 carbon atoms which has or does not have a substituent; n is 2 or 3; and p is a number in the range of 0.5 to 3 comprising the step of:

heating a rare earth carboxylate represented by the formula (II):

$$M(R^2-COO)_2.mH_2O \quad (II)$$

in which M and $R^2$ are the same as those defined above and m is a number satisfying the condition 0<m<4, together with an alkoxyalcohol represented by the formula (III):

$$R^1-O-(CH_2)_nOH \quad (III)$$

in which $R^1$ and n are the same as those defined above, to remove water together with the alkoxyalcohol by distillation.

2. The process of claim 1, wherein $R^2$ in the formula (II) is methyl.

3. The process of claim 1, wherein the alkoxy-alcohol represented by the formula (III) is at least one compound selected from the group consisting of 2-methoxyethanol, 2-ethoxyethanol, 1-methoxy-2-propanol, 1-ethoxy 2-propanol and 3-ethoxy-1-propanol.

4. The process of claim 1, wherein the rare earth carboxylate is a rare earth acetate and the rare earth acetate is heated together with ethoxyethanol so that water is distilled off together with the ethoxyethanol.

* * * * *